(12) United States Patent
Zimmerle et al.

(10) Patent No.: US 9,439,630 B2
(45) Date of Patent: Sep. 13, 2016

(54) NON-VISIBLE DETECTABLE MARKING FOR MEDICAL DIAGNOSTICS

(75) Inventors: Chris T. Zimmerle, Goshen, IN (US); Michael J. Pugia, Granger, IN (US); James A. Profitt, Goshen, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1055 days.

(21) Appl. No.: 12/674,944

(22) PCT Filed: Aug. 27, 2008

(86) PCT No.: PCT/US2008/074377
§ 371 (c)(1),
(2), (4) Date: Feb. 24, 2010

(87) PCT Pub. No.: WO2009/032657
PCT Pub. Date: Mar. 12, 2009

(65) Prior Publication Data
US 2011/0111522 A1    May 12, 2011

Related U.S. Application Data

(60) Provisional application No. 60/968,993, filed on Aug. 30, 2007.

(51) Int. Cl.
*G01N 33/543* (2006.01)
*A61B 10/00* (2006.01)
(Continued)

(52) U.S. Cl.
CPC ............. *A61B 10/007* (2013.01); *A61B 90/96* (2016.02); *G01N 33/558* (2013.01); *G01N 35/00732* (2013.01); *G01N 2035/00752* (2013.01); *G01N 2035/00772* (2013.01)

(58) Field of Classification Search
CPC .................... G01N 33/558; G01N 35/00732; G01N 2035/00752; G01N 2035/00772; A61B 2019/442
USPC ........................................................ 436/518
See application file for complete search history.

(56) References Cited

U.S. PATENT DOCUMENTS

| 5,408,535 A | 4/1995 | Howard, III et al. |
| 5,445,930 A | 8/1995 | Harada et al. |

(Continued)

FOREIGN PATENT DOCUMENTS

| EP | 0837320 B1 | 4/1998 |
| JP | 7190940 | 7/1995 |

(Continued)

OTHER PUBLICATIONS

Jürgen Fabian, "Near-Infrared Absorbing Dyes", Chem. Rev., 1992, pp. 1197-1226.

(Continued)

*Primary Examiner* — Mark Shibuya
*Assistant Examiner* — Pensee Do
(74) *Attorney, Agent, or Firm* — Kyle D. Petaja (57) ABSTRACT

Sample media for the analysis of analytes in a fluid test sample includes a carrier, at least one test field on the surface of the carrier including at least one reagent reactive with the analytes and capable of providing a detectable response. A non-visible bar code formed by at least two distinct non-visible marker fields is located on the carrier. The marker fields are configured to reflect electro-magnetic (EM) radiation within one or more ranges of non-visible wavelengths to form a coded sequence of reflectances correlated to identification of the sample media.

24 Claims, 4 Drawing Sheets

(51) Int. Cl.
  *G01N 33/558* (2006.01)
  *G01N 35/00* (2006.01)

(56) References Cited

U.S. PATENT DOCUMENTS

| | | |
|---|---|---|
| 5,453,505 A | 9/1995 | Lee et al. |
| 5,877,863 A | 3/1999 | Ross et al. |
| 5,945,341 A * | 8/1999 | Howard, III ............... 436/46 |
| 6,203,069 B1 | 3/2001 | Outwater et al. |
| 6,316,264 B1 | 11/2001 | Corey et al. |
| 6,770,487 B2 | 8/2004 | Crosby |
| 7,459,127 B2 | 12/2008 | Pugia et al. |
| 7,601,544 B2 | 10/2009 | Rehm |

FOREIGN PATENT DOCUMENTS

| | | |
|---|---|---|
| JP | 10132734 | 5/1998 |
| JP | 10267833 | 10/1998 |
| JP | 2001194368 | 7/2001 |
| JP | 2002303625 | 10/2002 |
| JP | 2004527755 | 9/2004 |

OTHER PUBLICATIONS

Notification of Reason for Refusal of corresponding Japanese Patent Application No. 2010-523099 issued on Jun. 26, 2012.
Corresponding PCT Application No. PCT/US2008/074377; International Search Report and Written Opinion date of mailing Nov. 24, 2008.

* cited by examiner

NON-VISIBLE DETECTABLE MARKING FOR MEDICAL DIAGNOSTICS

RELATED APPLICATION

This application claims the benefit of U.S. Provisional Application Ser. No. 60/968,993, entitled Infrared Detectable Marking For Medical Diagnostics, filed on Aug. 30, 2007, the contents of which are incorporated herein by reference in their entirety for all purposes.

BACKGROUND

1. Technical Field

This invention relates to automated reading of diagnostic reagents. More specifically, the present invention pertains to the placement of non-visible infrared ("IR") barcodes either within or adjacent to traditional color barcodes printed on reagent media to provide additional calibration and other information for a reagent lot.

2. Background Information

Many instruments have been developed to measure the presence and quantity of analytes in various biological samples such as, for example, urine, blood, saliva, extracts of mucus or tissue, etc. Typically, a sample liquid is applied to a surface, or carrier, containing reagents that react with the analyte. The reagents produce a detectable response that may be measured and related to the amount of analyte present in the sample.

Dry reagents are commonly used for diagnostics and may be read with an instrument, such as an optical reader and/or electrochemical reader. There are several conventional formats of dry reagent media including, for example, strip format, card format, and micro-fluidic chip format. There are also a number of possible configurations and within each particular format.

For example, sample media in the form of a test strip usually has one or more test areas spaced along the length thereof, with each test area being capable of undergoing a color change in response to contact with a liquid specimen. The liquid specimen usually contains one or more constituents or properties of interest. The presence and concentrations of these constituents or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist which employ reflectance photometry for reading test strip color changes. These instruments accurately determine the color change of a test strip within a particular wavelength range or bandwidth. Examples of such instruments include those sold under the CLINITEK® trademark (e.g., the CLINITEK ATLAS® and the CLINITEK® 500) by Siemens Healthcare Diagnostics Inc (Tarrytown, N.Y.) and/or as disclosed in U.S. Pat. Nos. 5,408,535 and 5,877,863, both of which are fully incorporated by reference herein. These instruments are typically used to detect colors associated with a urine specimen on a MULTISTIX® (Siemens) reagent strip, or on relatively large reagent strip rolls for high volume automated analysis such as provided by the CLINITEK ATLAS® Automated Urine Chemistry Analyzer.

In the past, color barcodes were used to convey reagent configuration to the read instrument. Generally, the color barcodes are placed on the dry reagent carrier and read by the instrument prior to analyzing the sample. Two methods are in known use for Point-of-Care instrumentation: 1) Large color bars (e.g., 0.2 inch) are used with the patterns of colors describing a reagent configuration; and 2) common black/white barcodes on test media such as cassettes or strips, in which the size/shape and sequence of the bars is used to encode the reagent configuration. The use of either one of these barcodes must substantially match software in the instruments, otherwise an error will result. The instruments are programmed to only recognize a number of barcode color configurations, and to adjust accordingly.

As technology in this field continues to advance, the need arises to convey additional and more sophisticated information to the read instrument. For example, newer read instruments have functionality and capabilities beyond those of their predecessors and require additional information to utilize that functionality. Accordingly, there is a need to add additional barcode configurations and colors to the color barcodes. However, this is not easily achieved as the addition of additional bars or colors would cause read errors in the older machines. The problem is one of backward compatibility. New reagent carriers or media with the additional information would generally cause read errors on older generation machines. Imprinting standard barcode information in a varied configuration or color would change the reflectance of the barcode and backward compatibility would be broken. Thus, it is generally required to either upgrade the instrument or the instrument's firmware, which disadvantageously tends to increase cost.

A need therefore exists for sample media that address the aforementioned drawbacks.

SUMMARY

In one aspect of the present invention, sample media for the analysis of one or more analytes in a fluid test sample includes a carrier, at least one test field on the surface of the carrier including at least one reagent reactive with the analytes and capable of providing a detectable response. A non-visible bar code formed by at least two distinct non-visible marker fields is located on the carrier. The marker fields are configured to reflect electro-magnetic (EM) radiation within one or more ranges of non-visible wavelengths to form a coded sequence of reflectances correlated to information concerning identification of the sample media.

In another aspect of the invention, sample media for the analysis of one or more analytes in a fluid test sample includes a carrier with at least one test field including a reagent reactive with the analyte or analytes being analyzed and capable of providing a detectable response. A first bar code is formed by at least two distinct marker fields on the carrier, the marker fields configured to reflect light within a range of visible wavelengths to form a coded sequence of reflectances correlated to information concerning identification of the sample media. A second bar code is formed by at least two distinct other marker fields on the carrier, the other marker fields configured to reflect light within a range of wavelengths in the infrared spectrum to form a coded sequence of reflectances correlated to other information concerning identification of the sample media.

Yet another aspect of the invention includes an automated method of reading sample media for the analysis of one or more analyte(s) in a fluid test sample. The method includes providing sample media having at least one test field which reflects light within a specific range of wavelengths, a first bar code formed by marker fields which reflect light within a range of visible wavelengths in a coded sequence correlated to information identifying the sample media, and a second bar code formed by other marker fields, which reflect light within a range of wavelengths in the infrared spectrum to form a coded sequence correlated to other information identifying the sample media. The method further includes introducing the sample media into a reading device configured to read the test fields, marker fields, and other marker fields, and which includes a light sensitive element capable of receiving and differentiating between the ranges of wavelengths at which the marker, other marker, and test fields reflect. The wavelength values reflected by the test, marker, and other marker fields are read, and the sequence of reflected range of wavelength values is correlated with predetermined information concerning the sample media.

The features and advantages described herein are not all-inclusive and, in particular, many additional features and advantages will be apparent to one of ordinary skill in the art in view of the drawings, specification, and claims. Moreover, is should be noted that the language used in the specification has been principally selected for readability and instructional purposes, and not to limit the scope of the inventive subject matter.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Embodiments of the present invention allow additional information to be written into the barcodes of various sample media, while providing for backward compatibility with legacy instruments which may have been unable or may not have been enabled to detect the new marking. In exemplary embodiments, this is achieved by having essentially two layers of information. The first layer may appear as a conventional visible (single or multiple color) barcode. This visible barcode may be used to provide reagent strip identification in a manner compatible with conventional diagnostic instruments/barcode scanners. The second layer may be a non-visible (e.g., IR or UV) barcode which is essentially invisible to a conventional instrument/barcode scanner, and which contains additional information that may be read by newer or upgraded read instruments. This allows the sample media (e.g., reagent strip) to appear one way to older instruments in order to provide current functionality, while also providing a higher resolution (e.g. more information) to be recorded in a way such that instruments capable of reading them can employ higher density barcode information. The function of these embodiments is thus to provide supplemental barcode functionality, such as by a barcode within a barcode functionality. This allows backward compatibility with older instruments (both in hardware and instrument software (firmware)) while at the same time allowing additional information to be encoded and read by new instrument hardware and/or software. This may avoid or delay the need for costly hardware and/or software upgrades, while at the same time providing additional feature benefits by encoding additional information such as calibration and lot information for the sample media.

Embodiments of the present invention thus do not require users to invest in upgrades to their conventional diagnostic instruments, since backward compatibility can be maintained. Furthermore, essentially a barcode within a barcode may be provided by these embodiments. A conventional visible color bar zone may contain within it additional information which is transparent (and hence backward compatible) to conventional legacy instrument software. This allows additional information to be encoded while keeping backward-compatibility intact.

Figure 1:
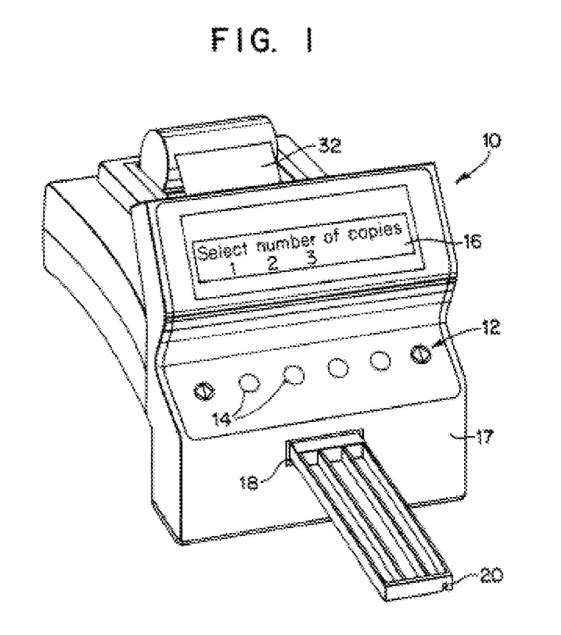
FIG. 1 is a perspective view of an exemplary medical diagnostic analyzer, which may incorporate embodiments of the present invention.
Figure 2:
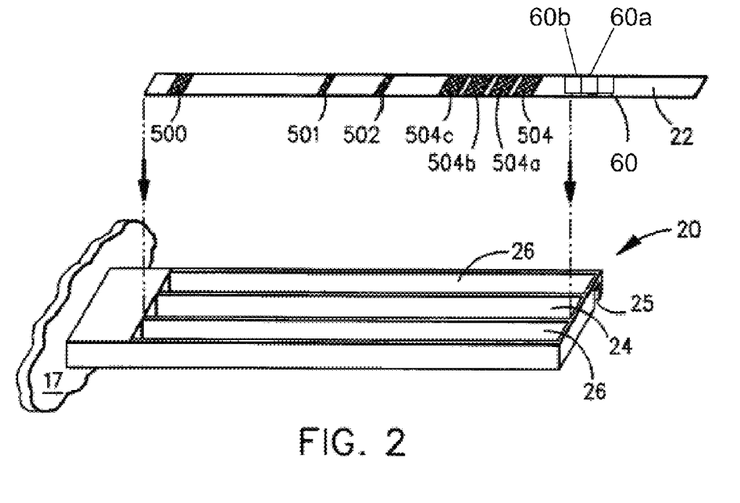
FIG. 2 is a perspective, partially exploded view of a portion of the analyzer of FIG. 1, with exemplary sample media in accordance with the present invention.

Turning now to FIG. 1, an exemplary reflectance spectrometer of the type that may be used in connection with the various embodiments hereof, is shown. Spectrometer 10 is capable of performing various tests, such as urinalysis tests, on sample media 22, such as a reagent chemistry or immunochemistry test strip. The spectrometer 10 has an integral keyboard 12 with a number of entry keys 14 that may be depressed by the user. A visual display 16 for displaying various messages relating to operation of the spectrometer 10 is disposed above the keyboard 12. Referring to FIGS. 1 and 2, the spectrometer 10 has a front face 17 and an opening 18 therein in which tray 20 for carrying a test strip 22 is retractably disposed. As shown, the tray 20 has a central channel 24 and two side channels 26 formed therein. The central channel 24 is sized to conform to the shape of the test strip 22. Examples of conventional spectrometers that may be modified in accordance with the teachings of the present invention include the CLINITEK® 50™, CLINITEK STATUS® and the CLINITEK ADVANTUS® instruments, all available from Siemens.

As is familiar to those skilled in the art, sample media 22 may include typical urine analysis strips, having paper pads disposed in spaced relation thereon, which are soaked in chemical reagents that react with a specimen sample to change color according to the medical condition of the patient, i.e., according to levels of various analytes in the sample. As used herein, the term 'analyte' refers to a constituent, or to a property (e.g., pH) of the sample. Examples of such media include the aforementioned MULTISTIX® test strips (e.g., in strip, card, or reel format). Alternatively, sample media 40 may include a conventional immuno-assay cassette, e.g., the CLINITEST® hCG cassette (Siemens), having chemical reagents that react to the sample to reveal a colored line or pattern of lines according to the medical condition of the patient.

Other suitable sample media may include conventional microfluidic devices which typically include a substrate having a series of narrow channels, e.g. on the order of microns in width, through which a fluid such as blood or urine may travel. The channels conduct the fluid to various test areas on the device. These devices enable various tests to be performed using only a small amount of fluid, e.g., using a small drop of liquid. Exemplary microfluidic devices are described in U.S. patent application Ser. No. 10/082,415 filed on Feb. 26, 2002 and entitled Method and Apparatus For Precise Transfer And Manipulation of Fluids by Centrifugal and/or Capillary Forces.

For convenience and clarity, various embodiments of the present invention are described as using sample media in the form of MULTISTIX® test strips 22, with the understanding that substantially any sample media of substantially any form factor, may be used without departing from the scope of the present invention. For example, sample media disposed within relatively large capacity cards or reels of the type used in the above-referenced CLINITEK® Atlas® instrument, may be desired for high volume sample processing. Embodiments of the present invention may also be beneficial when used with alternate media such as microfluidic devices or immuno-assay cassettes.

Referring to FIG. 2, the reagent test strip 22 has a carrier on which is disposed an absorbent material impregnated with reagents in specific locations referred to herein as test fields in which a color change, readable by the spectrometer, takes place as an indication of the presence and/or concentration of analyte in the test fluid. In particular embodiments, the carrier is elongated as shown, fabricated from an absorbent material which allows the analyte and labeled antibodies specific thereto to flow through it along with the fluid test sample and to form analyte/labeled antibody conjugates which can be captured in a specific capture zone thereof, to provide a spectrally detectable response.

When the end of the strip 22 (e.g., up to label 500) comes into contact with a fluid test sample such as urine, the liquid migrates up the strip, due to the absorbent nature of the carrier material, to cause a color change in test fields 501, 502.

To carry out an analysis of a liquid test sample, such as a urinalysis, the reagent strip 22 is dipped into a urine sample to be tested up to label 500 and then placed in the central channel 24 of the spectrometer tray 20. The operator presses one of the start keys 14 to initiate testing which causes the tray to be automatically retracted into the spectrometer 10. The strip includes a visible bar code formed by marker fields 504, 504a, 504b and 504c, and, in accordance with the teachings of the present invention, may optionally bear non-visible barcode, formed by non-visible marker fields 60, 60a, etc. Once the test strip is retracted into the spectrometer, the apparatus reads the bar code by analysis of its spectral reflectance values. For example, the marker field 504 may be white, with the spectrometer interprets as representing a conventional dry phase chemistry reagent strip. Another color could be used to indicate that a different reagent system, e.g. immunochromatographic, was being read. The instrument 10 may be programmed to read the other marker fields; e.g. 504a, 504b and 504c, to correlate the sequence of reflected wavelengths with other preprogrammed information concerning the test strip. Thus, the visible marker fields 504, 504a, etc., form a visible barcode that serves to automatically ensure that the strip is analyzed in the proper manner by spectrometer 10.

It should be noted that not all of the marker fields 504, 504a, 504b, 504c of the "visible" barcode need to reflect light in the visible spectrum. Rather, at least one of these marker fields may reflect in the non-visible region of the spectrum. Moreover, it should be recognized that the marker fields of the visible barcode may be in the form of a conventional black and white barcode, e.g., in which the marker fields all reflect the same color, but encode information by their size/shape and relative location/sequence, as discussed herein.

Where used in this disclosure, the term "visible light" and/or "visible electro-magnetic (EM) radiation" refers to the portion of the electromagnetic spectrum that is visible to the human eye, and which corresponds to the range of EM wavelengths of about 400 to about 700 nm. The term "non-visible" and/or "non-visible electro-magnetic radiation" refers to the portion of the electromagnetic spectrum outside the range of EM wavelengths of visible light.

Figure 3:
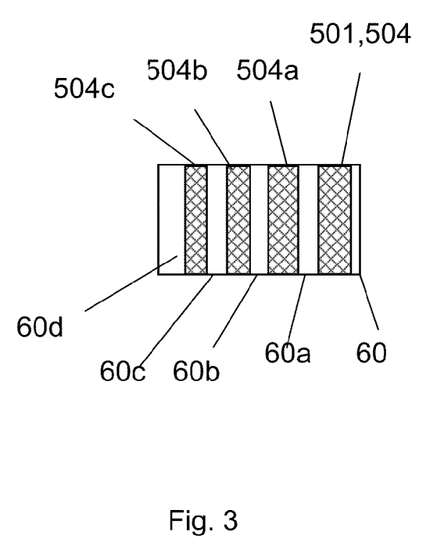
FIG. 3 is a schematic plan view, on an enlarged scale, of a portion of the sample media of FIG. 2.
Figure 4:
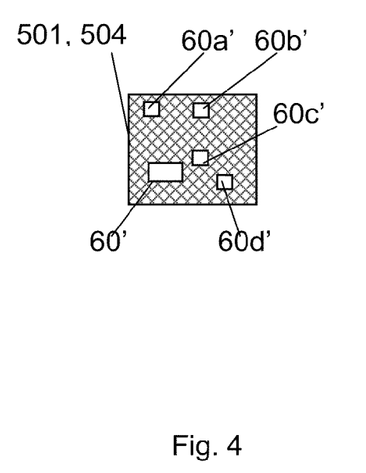
FIG. 4 is a view similar to that of FIG. 3, of an alternate embodiment of sample media of the present invention.

Referring now to FIGS. 2-4, aspects of the various embodiments of the invention will be described in greater detail. Exemplary non-visible barcodes may be formed by non-visible marker fields sized and shaped to form a one dimensional (1D) pattern, such as by marker fields 60, 60a, 60b, etc. of FIGS. 2 and 3. Alternatively, non-visible barcodes may be formed by non-visible marker fields sized and shaped to form a two dimensional (2D) pattern, such as by non-visible marker fields 60', 60a', 60b', etc., of FIG. 4. The non-visible barcodes are thus formed by at least two distinct non-visible marker fields 60, 60a, etc., or 60', 60a', etc., disposed on the carrier, the non-visible marker fields being capable of reflecting electro-magnetic (EM) radiation to form a coded sequence which sequence correlates to information concerning identification of the test strip.

The non-visible barcodes may be placed adjacent to the conventional visible barcode. Alternatively, an entire non-visible barcode may be interspersed and/or superposed with the traditional visible barcode. For example, the non-visible barcode may be placed adjacent to the visible barcode as shown in FIG. 2, for use in conjunction with, or as an alternative to, the visible barcode. This permits older instruments that are incapable of detecting non-visible (e.g., IR or UV) barcodes to respectively read only the visible barcode (or alternatively, a blank barcode in the event no visible barcode is provided). The non-visible barcode lies outside the normal visible spectrum so that cannot be observed by the instrument under normal light conditions.

Alternatively, as shown in FIGS. 3 and 4, the non-visible marker fields of these barcodes may be interspersed among, or superposed with, the visible marker fields 504, etc., and/or test fields 501, etc., of the sample media. For example, as shown in FIG. 3, an non-visible barcode formed by non-visible marker fields 60, 60a, 60b, 60c and 60d is superposed and/or interspersed among the visible marker fields 504, 504a, 504b, 504c of the visible barcode in a 1D pattern. (It should also be recognized that these non-visible marker fields may be similarly superposed and/or interspersed among the test fields 501, etc.) In another example shown in FIG. 4, a non-visible barcode formed by marker fields 60', 60a', 60b', 60c' and 60d' is disposed in a 2D pattern. Moreover, one or more of these non-visible marker fields may be interspersed among the visible marker fields or test fields, or may be superposed with one or more visible marker fields 504, and/or test fields 501, as shown.

It is understood that in various embodiments, the dye(s) used in marker fields 60, 60', etc., should be as visibly transparent as possible (i.e., transparent in the visible spectrum) to help ensure that non-visible barcode does not to interfere with reading of the visible barcode and/or test fields. Although complete visible transparency may not be required in all applications, substantial visible transparency may be particularly desirable for embodiments in which the non-visible barcode is interspersed or superposed with optically visible marker or test fields, as shown in FIGS. 3, 4.

The embodiments discussed herein thus provide for a new separate barcode, including in the form of a barcode within a barcode and/or within one or more test fields, as shown in FIGS. 3, 4, to allow for the encoding of more complex information than heretofore provided using visible marker fields. As mentioned above, examples of the type of information that may be encoded into the visible and non-visible barcodes may include the analyte and other information relating to the analyte for which the sample media is designed to test, location of reflecting areas on the sample media, the age of the sample media, the reactivity of the sample media, for which the media is intended to test, the lot and/or production batch of the sample media, calibration information which relates to the production batch from which the sample media was obtained, and combinations thereof.

As discussed hereinabove, the non-visible marker fields may be formed by the use of dyes and the like, which reflect EM radiation in nominally any wavelength range outside of the visible spectrum. For example, materials that reflect in the infrared (IR) and/or ultraviolet (UV) wavelengths may be used. In particular embodiments, IR dyes may be used.

There are many known infrared dyes that are commercially available on the market that are suitable for purposes of this invention. As discussed herein, infrared refers generally to the spectrum of wavelengths greater than about 750 nm, but particular embodiments, greater than about 800 nm. Furthermore, there are many methods of application of infrared dye that can be used with the present invention. For example, the IR barcode may be conveniently formed by printing the infrared dye on the sample media in any convenient manner such as by ink jet printing, screen printing, or by various deposition processes using a mask to control the locations on the carrier at which the infrared dye is deposited. Alternatively, the infrared dye may be applied by spray or other deposition without a mask, and suitable means such as a laser may then be used to remove undesired portions of the dye so that the remaining infrared dye forms a desired barcode format. In this regard, it should be recognized that the barcodes shown and described herein may be configured to encode information based on any number of various parameters, including size, shape, location on the carrier, and/or the particular wavelength(s) of EM reflectance. For example, as described herein, barcodes such as the visible barcode of FIGS. 2 and 3 may be encoded primarily by varying the colors of marker fields 504, 504a, etc. Alternatively, barcodes such as the non-visible barcode of FIG. 3 may be encoded based on the size (e.g., in the longitudinal direction of the carrier) and relative longitudinal location/sequence of the variously sized marker fields on the carrier. Still further, in addition to size, encoding may be effected based on both longitudinal and transverse location of the marker fields on the carrier, to form a 2D pattern such as shown with respect to the non-visible barcode of FIG. 4. It should be further recognized that any number of mutually distinct IR (or UV) wavelengths may be used in connection with the marker fields of the non-visible barcodes in order to provide still further encoding options.

An IR dye useful in the present invention has a strong absorbance in the infrared region. The identity of the IR dye is not otherwise limited. As mentioned above, desired IR dyes lack a visible color because such dyes have a low tendency, if any tendency at all, to interfere with measurement of the color change of the strip, and, accordingly, should not adversely affect performance of the test strip. In embodiments wherein the IR dye is incorporated into a test pad, the IR dye cannot adversely affect the reagent incorporated into the test pad or adversely affect an interaction between the analyte of interest and reagent present in the test pad.

Infrared (IR) radiation is that portion of the electromagnetic spectrum between the visible and microwave regions. In that broad region, the portion between about 700 nm and about 2500 nm is the near-infrared (i.e., near-IR or NIR). The portion of the electromagnetic spectrum visible to man is between about 400 nm and 700 nm. Many different classes of dyes are known to have absorbances in the IR, and particularly the NIR region. Among the IR dyes are phthalocyanine and naphthalocyanine compounds, metal complex dyes (such as dithiolene metal complex dyes), and the large class of polymethine dyes, including the cyanine dyes. Other classes of NIR dyes include the di- and triphenylmethane dyes, quinone dyes, certain azo dyes, and charge transfer and charge resonance dyes. Additional IR dyes are described and disclosed in J. Fabian, Chem. Rev., 92, pp. 1197-1226 (1992), incorporated herein by reference.

In general, any IR dye, and especially any NIR dye, may be used in the present invention. Choice of a specific dye depends on the optical system used for its detection, compatibility with the method used for its application to the test strip, stability, and cost. An IR dye having a strong absorbance in the range of 825-855 nm is preferred. It is also desirable that the dye lacks a visible color. Generally, a desired dye has an absorbance in the visible region (i.e., 400-700 nm) less than 20% that of the absorption maximum of the dye in the NIR region. Other desired dyes have visible absorbances of less than 10%.

The following Table 1 illustrates nonlimiting examples of useful IR dyes. Other useful IR dyes are known to persons skilled in the art. The IR dye is present on the test strip in an amount of about 0.05 to about 0.3, and in some embodiments, about 0.07 to about 0.2 microgram per strip. In still other embodiments, the IR dye is present on the test strip in an amount of about 0.1 to about 0.2 micrograms per strip, either on or off a test or marker field.

TABLE 1

Dye IR Absorbance Maximum Visible Absorbance 1. 5,5'-dichloro-11-diphenylamino-3,3'-diethyl-10,12-ethylene-thiatricarbocyanine perchlorate (IR-140)[1]
2. 3-(5-carboxypentyl)-2-[2-[3[[3-(5-carboxypentyl)-1,3-dihydro-1,1-dimethyl-2H-benz[e]indol-2-ylidene]ethylidene]-2-(2-sulfoethylthio)-1-cyclohexene-1-yl]ethenyl]1,1-dimethyl-1H-benz[e] indolinium, inner salt (DTO-108)[2]
3. 3-(5-carboxypentyl)-2-[2-[3-[[3-(5-carboxypentyl)-1,3-dihydro-1,1-dimethyl-2H-benz[e]indol-2-ylidene]ethylidene]-2-(n-hexylthio)-1-cyclohexen-1-yl]ethenyl]-1,1-dimethyl-1H-benz[e]indolium, inner salt (DTO-141)[2]
4. Copper (II) 5,9,14,18,23,27,32,36-octabutoxy-2,3-naphthalocyanine
5. 5,9,14,18,23,27,32,36-octabutoxy-2,3-naphthalocyanine
6. IR-165 (N,N,N[1],N[1]-tetrakis (p-dibutylaminophenyl)-p-benzoquinone bisaminium hexafluoroantimonate)[3]

[1]Available from Aldrich Chemical Co., Milwaukee, WI;
[2]These dyes were prepared from a reaction between a precursor disclosed in Lee et al. U.S. Pat. No. 5,453,505, and mercaptoethane sulfonic acid sodium salt or hexanethiol according benzoquinone to the general method disclosed in Harada et al. U.S. Pat. No. 5,445,930. The precursor is known by Chemical Abstract Service (CAS) registry number [174829-19-7].
[3]Available from Sperian, Smithfield, R. I.

Sample media of the present invention can be configured either as single analyte media (to assay only for a single analyte) or as multiple analyte media (to assay for several unknowns or analytes simultaneously), and in nominally any form factor including strip, card, cassette, etc., as discussed hereinabove. The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices includes filter paper, sponge materials, cellulose, wood, woven and nonwoven fabrics, and the like. Nonbibulous matrices include glass fiber, polymeric films, and preformed or microporous membranes. Other suitable carrier matrices include hydrophilic inorganic powders, such as silica gel, alumina, diatomaceous earth, and the like; argillaceous substances; cloth; hydrophilic natural polymeric materials, particularly cellulosic material, like cellulosic beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions, or a mixture of chemical compositions. The matrix also can vary in regards to smoothness and roughness combined with hardness and softness. However, in every instance, the carrier matrix must include a hydrophilic or absorptive material. The carrier matrix is most advantageously constructed from bibulous filter paper or nonbibulous polymer films.

The resulting sample media is used in accordance with methods well known in the art. As stated above, the assay for a predetermined analyte is performed by contacting the test sample with the sample media. The media can be dipped into the test sample, or the test sample can be applied to the sample media. The resulting change in color of the test field(s) demonstrates the presence of analyte and the resulting color transition can be measured spectrophotometrically to provide a quantitative assay for the concentration of analyte in the test sample.

An exemplary embodiment of a method of the present invention is shown and described with respect to the following Table 2. As shown, an automated method of reading sample media for the analysis of one or more analyte(s) in a fluid test sample includes, at 100, providing sample media 22 having one or more test fields on its surface, a first bar code formed by at least two distinct visible marker fields which reflect visible light in a coded sequence which correlates to information concerning identification of the sample media, and a second bar code formed by at least two distinct other marker fields, which reflect light within the IR (infrared) spectrum to form a coded sequence of spectral regions which correlate to other information concerning identification of the test strip. At 102, the sample media is introduced into a reading device 10 which is configured to read the test fields, marker fields, and other marker fields, the reading device including a light sensitive element capable of receiving and differentiating between the ranges of wavelengths at which the marker, other marker, and test fields reflect. At 104, the wavelength values reflected by the test, marker, and other marker fields are individually read by the reading device 10. At 106, the sequence of reflected range of wavelength values is correlated with predetermined information concerning the sample media.

TABLE 2

| | |
|---|---|
| 100 | providing sample media 22 having at least one test field, a first bar code formed by at least two distinct marker fields which reflect visible light in a coded sequence which correlates to information concerning identification of the sample media, a second bar code formed by at least two distinct other marker fields which reflect light within the IR (infrared) spectrum to form a coded sequence correlated to other information concerning identification of the test strip; |
| 102 | introducing the sample media into a reading device configured to read the test fields, marker fields, and other marker fields, and which includes a light sensitive element capable of receiving and differentiating between the ranges of wavelengths at which the marker, other marker, and test fields reflect; |
| 104 | reading the test, marker, and other marker fields; and |
| 106 | correlating the sequence of spectral reflectance values read from the marker fields and the other marker fields, with predetermined information concerning the sample media. |

The following illustrative examples demonstrate certain aspects and embodiments of the present invention, and are not intended to limit the present invention to any one particular embodiment or set of features.

EXAMPLES

Figure 5A:
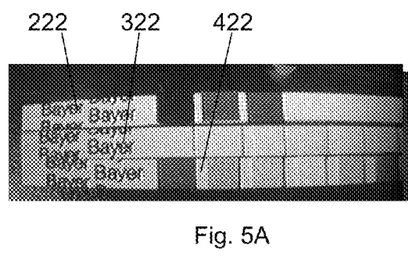
FIGS. 5A and 5B are photographs of additional embodiments of sample media of the present invention.
Figure 5B:
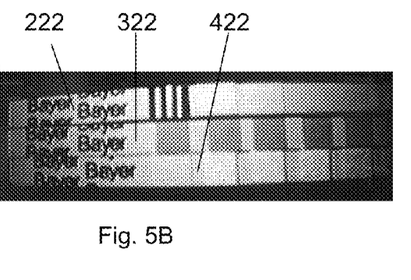

Images of three test strips were captured by a camera in black and white mode under visible light (FIG. 5A) and under an IR LED (FIG. 5B). The upper strip 222 included visible color test fields of the type used on the MULTSTIX® Microalbumin (Siemens) test strip. An exemplary 1D nonvisible barcode was formed by depositing IR dye onto the left-hand (visibly black) test field thereof, using a laser to burn off portions of the dye to form a pattern of IR marker fields of varying size. As shown, this test field appears black under normal visible light in FIG. 5A, while revealing a higher resolution striped barcode when viewed under an infrared LED as in FIG. 5B.

An IR dye was also applied to visibly white test fields of a conventional MULTISTIX® test strip 322. These test fields appear white when viewed under normal lighting as shown in FIG. 5A, and appear visibly darker under IR lighting as shown in FIG. 5B.

The bottom strip 422 is a conventional MULTISTIX® SG (Siemens) test strip, having conventional visibly colored test fields. This test strip was not provided with any IR dye to serve as a control. The visibly color of the test fields appears under normal light as shown in FIG. 5A, while no color is visible under the IR light of FIG. 5B.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. Sample media for the analysis of one or more analytes in a fluid test sample which comprises:
    a carrier;
    a first test field and a second test field, the first test field and the second test field being disposed on the surface of the carrier including at least one reagent reactive with the one or more analytes and capable of providing a detectable response, the first test field being the closest test field to a distal end of the carrier;
    a non-visible bar code formed by at least two distinct non-visible marker fields disposed on the carrier, the non-visible marker fields are visibly transparent on the carrier and are configured to reflect electro-magnetic (EM) radiation within one or more ranges of non-visible wavelengths to form a coded sequence of reflectances which sequence correlates to information concerning identification of the sample media, the non-visible bar code being (1) separate from the first test field and the second test field and (2) disposed in between the first test field and the first distal end of the carrier; and
    a visible bar code formed by at least two distinct visible marker fields disposed on the carrier, the visible marker fields being configured to reflect EM radiation at ranges of wavelengths in the visible light spectrum and predetermined to form a coded sequence of reflectances which sequence correlates to other information concerning identification of the sample media, the visible bar code being (1) separate from the first test field and the second test field and (2) disposed in between the first test field and the first distal end of the carrier.

2. The sample media of claim 1, wherein the non-visible marker fields are configured to reflect EM radiation at mutually distinct ranges of wavelengths from one another.

3. The sample media of claim 1, wherein the carrier is elongated and comprises an absorbent material configured to allow the analyte and labeled antibodies specific thereto to flow through it along with the fluid test sample and to form analyte/labeled antibody conjugates which can be captured in a specific capture zone thereof.

4. The sample media of claim 3, wherein the first test field and the second test field are configured to capture either the labeled antibody or the analyte/labeled antibody conjugate and to provide a spectrally detectable response.

5. The sample media of claim 1, wherein the reagent is capable of interacting with a predetermined analyte to provide a spectrally detectable response.

6. The sample media of claim 1, wherein the non-visible bar code comprises an infrared (IR) barcode formed by at least two distinct IR marker fields disposed on the carrier, the marker fields configured to reflect EM radiation at ranges of wavelengths within the IR spectrum.

7. The sample media of claim 6, wherein the IR marker fields are configured to reflect wavelengths within the IR spectrum which are mutually distinct from one another.

8. The sample media of claim 6, wherein the infrared barcode is configured to reflect light in the spectrum of wavelengths greater than about 750 nm.

9. The sample media of claim 8, wherein the infrared barcode is configured to reflect light in the spectrum of wavelengths greater than about 800 nm.

10. The sample media of claim 6 wherein about 0.05 to about 0.3 micrograms of infrared dye are positioned on the sample media and comprise the infrared barcode.

11. The sample media of claim 6 wherein the infrared barcode absorbs infrared radiation at least at one infrared wavelength.

12. The sample media of claim 11 wherein the infrared barcode lacks a visible color.

13. The sample media of claim 6 wherein infrared dye used in the infrared barcode is selected from the group consisting of: 5,5'-dichloro-11-diphenylamino-3,3'-diethyl-10,12-ethylenethiatricarbocyanine perchlorate;
    3-(5-carboxypentyl)-2-[2-[3[[3-(5-carboxypentyl)-1,3-dihydro-1,1-dimethyl-2H-benz[e]indol-2-ylidene]-ethylidene]-2-(2-sulfoethylthio)-1-cyclohexene-1-yl]ethenyl]1,1-dimethyl-1H-benz[e] indolinium;
    3-(5-carboxypentyl)-2-[2-[3-[[3-(5-carboxypentyl)-1,3-dihydro-1,1-dimethyl-2H-benz[e]indol-2-ylidene]-ethylidene]-2-(n-hexylthio)-1-cyclohexen-1-yl]-ethenyl]-1,1-dimethyl-1H-benz[e]indolium;
    copper (II) 5,9,14,18,23,27,32,36-octabutoxy-2,3-naphthalocyanine;
    5,9,14,18,23,27,32,36-octabutoxy-2,3-naphthalocyanine;
    IR-165 (N,N,N$^1$,N$^1$-tetrakis (p-dibutylaminophenyl)-p-benzoquinone bisaminium hexafluoroantimonate); and mixtures and combinations thereof.

14. The sample media of claim 1, wherein the visible marker fields are configured to reflect EM radiation at ranges of wavelengths that are mutually distinct from one another.

15. The sample media of claim 1, wherein the non-visible bar code is disposed adjacent the visible bar code.

16. The sample media of claim 1, wherein the non-visible bar code is superposed with at least one of the visible bar code.

17. The sample media of claim 1 wherein at least the non-visible marker fields are sized and shaped to form a one-dimensional pattern on the carrier.

18. The sample media of claim 1 wherein at least the non-visible marker fields are sized and shaped to form a two-dimensional pattern on the carrier.

19. The sample media of claim 1 wherein at least one marker field of the visible bar code reflects in the non-visible region of the spectrum.

20. The sample media of claim 1 wherein at least one of the information and other information, is selected from the group consisting of the analyte for which the sample media is designed to test, location of reflecting areas on the media, the media's age, the media's reactivity, and combinations thereof.

21. The sample media of claim 20 wherein at least one of the information and other information relates to the analyte for which the media is intended to test.

22. The sample media of claim 1 wherein at least one of the information and other information comprises production batch information from which the sample media was obtained, and calibration information which relates thereto.

23. The sample media of claim 1, selected from the group consisting of test strips, cards, reels, immuno-assay cassettes, and microfluidic devices.

24. Sample media for the analysis of one or more analytes in a fluid test sample which comprises:
    a carrier;
    a first test field and a second test field, the first test field and the second test field being disposed on the surface of the carrier including at least one reagent reactive with the analyte or analytes being analyzed and capable of providing a detectable response, the first test field being the closest test field to a distal end of the carrier;
    a first bar code formed by at least two distinct marker fields disposed on the carrier, the marker fields configured to reflect light within a range of visible wavelengths to form a coded sequence of reflectances which correlate to information concerning identification of the sample media, the first bar code being (1) separate from the first test field and the second test field and (2) disposed in between the first test field and the first distal end of the carrier;

a second bar code formed by at least two distinct other marker fields disposed on the carrier, the other marker fields are visibly transparent on the carrier and are configured to reflect light within a range of wavelengths in the infrared spectrum to form a coded sequence of reflectances which correlate to other information concerning identification of the sample media, the second bar code being (1) separate from the first test field and the second test field and (2) disposed in between the first test field and the first distal end of the carrier.

* * * * *